United States Patent [19]

Kinnamon

[11] 4,187,300

[45] Feb. 5, 1980

[54] USE OF PHOSPHONIUM SALTS IN TREATMENT OF AFRICAN TRYPANOSOMIASIS

[75] Inventor: Kenneth E. Kinnamon, Silver Spring, Md.

[73] Assignee: The United States of America as represented by the Secretary of the Army, Washington, D.C.

[21] Appl. No.: 971,124

[22] Filed: Dec. 20, 1978

[51] Int. Cl.$^2$ .............................................. A61K 31/66
[52] U.S. Cl. ..................................................... 424/198
[58] Field of Search ........................................ 424/198

[56] References Cited

U.S. PATENT DOCUMENTS

| | | | |
|---|---|---|---|
| 3,642,989 | 2/1972 | Basel et al. | 424/198 |
| 3,662,065 | 5/1972 | Balske | 424/198 |

*Primary Examiner*—V. D. Turner
*Attorney, Agent, or Firm*—William G. Gapcynski; Sherman D. Winters; Werten F. W. Bellamy

[57] ABSTRACT

Subject triaryl benzyl phosphonium salts afford new means for the treatment of African trypanosomiasis. Such compounds may be administered safely to infected animals either parenterally or orally.

7 Claims, No Drawings

USE OF PHOSPHONIUM SALTS IN TREATMENT OF AFRICAN TRYPANOSOMIASIS

BACKGROUND OF THE INVENTION

This invention relates to a method of treating the African trypanosomiasis disease usually referred to as sleeping sickness when it occurs in man. Specifically, this invention relates to the discovery that certain phosphonium salts possess anti-trypanosomal activity.

African sleeping sickness is an endemic and occasionally epidemic infectious disease which is progressive and usually fatal if untreated. The disease is caused by either of two protozoan species, *Trypanosoma gambiense* or *T. rhodesiense*, and transmitted by the bite of the tsetse fly. The disease is confined to the African Continent and a few adjacent islands, and even then is restricted to the tropics. It has had continuing effect on the history of tropical Africa. For example, it is estimated that in an area of over 2,000,000 square miles, draft animals are virtually absent. Furthermore, the protein malnutrition of tropical Africa has been traced in part to the partial vegetarianism enforced on a society in which it is impossible to rear the common comestible animals owing to diverse trypanosome infections of man's animals.

Although partially effective drugs are available for therapy and prophylaxis, all presently employed drugs have very serious, toxic side effects. Less toxic, more effective chemical agents are needed urgently.

SUMMARY OF THE INVENTION

It has been discovered that certain phosphonium salts have a remarkable toxic effect on *Trypanosoma rhodesiense*. Through extensive tests on laboratory animals those compounds have been proven to be effective trypanocides. While the medicinal use of certain phosphonium salts for control of non-protozoal infections is known, effective worth against protozoal infections was not described prior to this invention. See for example, U.S. Pat. No. 3,957,978 which is directed to the use of certain phosphonium salts to control worms in animals. Specifically, it has been discovered that triaryl benzyl phosphonium halides (structure I) exhibit anti-trypanosomal activity. In subject phosphonium salts the aryl [i.e. (AR)] groupings may be the same or different.

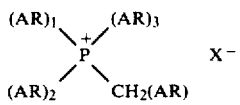

Accordingly, it is an object of this invention to provide a new anti-trypanosomal medicinal treatment.

It is another object of this invention to provide a class of compounds which when administered subcutaneously or orally can provide a cure of *T. rhodesiense* infections.

It is still another object to provide triaryl benzyl phosphonium halides wherein the aryl substituents are phenyl or substituted phenyl moieties which are active against *T. rhodesiense* infections.

These and other objects will become readily apparent with reference to the following description.

Compounds having the structure (I) may be administered perorally or parenterally to achieve anti-trypanosomal effects. Non-restrictive examples of the salt form [i.e., anionic portion of structure (I)] include the common halides, however other salt forms may be prepared therefrom. Thus, the chloride salt may be converted into a nitrate, or phosphate, or sulfate, or sulfamate through use of an appropriate resin. Organic salts of (e.g.) pamoic acid, citric acid, and suramin may also be formed.

When administered in oral dosage forms, subject anti-trypanosomal agents may be incorporated into tablets (single or multi-layer, coated or uncoated), capsules, dragees, and the like. The formulation of such oral dosage forms may advantageously include optional excipients such as lactose, precipitated chalk, dibasic calcium phosphate, microcrystalline cellulose derivatives, maize starch, talc, calcium stearate, or like adjuvant substances whose identity and use are well known in the pharmaceutical compounding art. For parenteral administration, aqueous or oily solutions of these phosphonium salts may be used in a wide range of concentrations. In certain instances, advantage may be gained with use of aqueous suspensions such as may be obtained with ethoxylated sorbitan fatty acid esters, optionally with addition of thickeners such as carboxymethyl cellulose or polyethylene glycol.

In summary, it has been discovered that triaryl benzyl phosphonium halides wherein the aryl substituent is a phenyl or substituted phenyl moiety, exhibit anti-trypanosomal activity against *Trypanosoma rhodesiense* infections and are therefore effective agents in the treatment of African trypanosomiasis.

The invention may be embodied in other specific forms without departing from the spirit or essential characteristics thereof. The present embodiment, is therefore, to be considered in all respects as illustrative and not restrictive, the scope of the invention being indicated by the appended claims rather than by the foregoing description, and all changes which come within the meaning and range of equivalency of the claims are, therefore, intended to be embraced therein.

DETAILED DESCRIPTION OF THE INVENTION

The method for synthesis of phosphonium salts of structure (I) is well known in the literature, and it may be exemplified in the following recent references: J. Novotny, et al., J. Pharm. Sci., 62, 910-913 (1973); W.E. McErven, et al., J. Org. Chem., 41, 1684-1690 (1976). In general, here it consists in causing an appropriate triaryl phosphine to react with RCH$_2$X (wherein R is aryl grouping and X being halogen) in a suitable solvent, usually one of low polarity. The resulting crude phosphonium salt is crystallized to provide the pure compound. A number of such phosphonium salts are available from suppliers of organic compounds for research owing to the fact that they find use in the so-called Wittig reaction: cf. A. Maercker, in Organic Reactions, vol. 14, pp. 270-490 [John Wiley & Sons, New York, 1965].

Should other salts be desired, the benzyl triarylphosphonium halides may be converted into a diversity of other salts. Ion exchange resins may find use for convenient transformation of the halides into other salts, such as nitrates, sulfates, sulfamates, citrates or phosphates. Less soluble salts (such as pamoates or suraminates) may be prepared by double decomposition of the halide and an alkali metal salt of the requisite acid.

Methods

The activity of the compounds of this invention was determined according to the procedure outlined in the article entitled "Screening Large Numbers Of Compounds In A Model Based On Mortality Of *Trypanosoma rhodesiense* Infected Mice," The American Journal of Tropical Medicine and Hygiene, Volume 25, No. 3, pages 395–400 (1966). To summarize, however, experiments were conducted with the Wellcome CT strain of *Trypanosoma rhodesiense* originally isolated in 1934. The test system is patterned after the one developed and employed in testing of compounds for activity against *Plasmodium berghei* malaria [see Osdene, et al., New Series of Potential Antimalarial Agents, J. Med. Chem., 10, 431–434 (1967)]. The test system is based on comparisons of responses to test compounds by ICR/HA Swiss mice infected with the strain as expressed in mean survival times compared with mean survival times of untreated controls.

By using a standard inoculum of the trypanosomes, it is possible to produce a uniform disease fatal to 100% of untreated animals within four to six days with a mean survival time of 4.45±0.24 days. Test animals, six weeks of age, of the same sex and weighing 30–32 grams receive an intraperitoneal injection of 0.5 ml of a 1:50,000 dilution of heparinized heart blood drawn from donor mice infected with *T. rhodesiense* 3 days earlier. Compounds to be tested are given as a single dose in peanut oil mull about 2 hours after parasite inoculation. Each test basically comprises five mice per drug dose level, with 20 infected untreated (negative) controls, and 20 infected positive controls. Positive controls are mice infected and treated at 40 mg per kg with either stilbamidine di-isethionate or 2-hydroxystilbamidine di-isethionate. Test compounds are initially tested by a subcutaneous route of administration, and may subsequently be tested by an oral route of administration. In each experiment, test compounds are administered in graded dosages.

Deaths prior to the fourth day (when untreated controls begin to die) are regarded as not related to the infection and are scored as "toxic deaths." Treated animals are kept under observation for 30 days. Survivors at the end of this time are considered cured. An increase of 100% in mean survival time over control animals is considered as a minimum effective response. In calculating mean survival times, toxic deaths and 30 day survivors are not included.

The compounds tested were administered as a single dose, subcutaneously or orally at a concentration of 3.2% in peanut oil (USP peanut oil obtained from Durkee Foods, Coral Gables, Florida) after the compound had been ground to a fine powder with mortar and pestle.

EXAMPLES

In each of the following Examples, the results of tests as described above are compiled in tabular form. In all tests reported, at least a subcutaneous route of administration for the compounds was used, with the dosages reported in mg/kg body weight of mice infected with *T. rhodesiense* as described above. An increase of mean survival time of 100% for the test animals over the control animals was basis for assessment of antitrypanosomal activity. "Cures" were indicated when animals survived more than 30 days. Toxic effects of drugs were considered as cause of deaths when test animals died before controls. When details have been recorded (Tables II, III, V, and VI), MSTT indicates mean survival time in days for test animals; MSTC, mean survival time (days) for controls; T-C, the difference in days between MSTT and MSTC; MSTX, the mean survival time (days) for first death to occur; and TOX indicates the number of deaths which occurred in test animals prior to those in controls.

Table I covers Examples 1–11, which are triphenyl benzyl (or, 8-quinolyl methyl in Example 11) phosphonium salts together with data on their activity in the T. rhodesiense test system. In each of those Examples, and Example 12, triphenyl phosphine and an appropriate RCH$_2$X (usually, a benzyl halide type) were caused to react in suitable solvent to produce the desired phosphonium salt. Ordinarily, a solvent of low polarity such as benzene, xylene, or diethyl ether was preferred as reaction medium. The phosphonium salt was collected and crystallized appropriately to afford good recovery of pure compound. Example 13 relates to 3,4-dichlorobenzyl-tris(3-methylphenyl)phosphonium chloride, which was made from tris(3-methylphenyl) phosphine and 3,4-dichlorobenzyl chloride. Testing data for Examples 12 and 13 are shown in Tables II and III.

Table IV relates to benzyl triaryl phosphonium salts (Examples 14–18) together with data on their evaluation in the *T. rhodesiense* test. In those Examples, and Examples 19 and 20, benzyl chloride was interacted with the appropriate triaryl phosphine type to produce the desired phosphonium chloride, following the method outlined above. Testing data for Examples 19 and 20 are given in Tables V and VI.

Table I.

Benzyl Triphenyl Phosphonium Salts Having Activity Against *Trypanosoma rhodesiense* Infections of Mice
(AR)$_3$ PCH$_2$R X$^-$

| Example Number | AR | R | X | Route$^a$ | 424 | 212 | 106 | 53 | 26.5 | 13.3 | 6.65 |
|---|---|---|---|---|---|---|---|---|---|---|---|
| 1 | C$_6$H$_5$ | C$_6$H$_5$ | Br | SC | 0/5(5T)$^b$ | | 0/10(10T) | 0/5* | 1/10 | 0/5 | 0/5 |
|  |  |  |  | O |  | 0/5(5T) | 6/10 | 0/5 | 0/10 | 0/5 |  |
| 2 | C$_6$H$_5$ | C$_6$H$_4$Cl(2) | Cl | SC | 0/10(10T) | 0/5(5T) | 2/10(8T) | 2/5(1T) | 6/10 | 0/5 |  |
|  |  |  |  | O | 0/10(10T) | 0/5(5T) | 0/10* | 0/5 | 0/10 | 0/5 |  |
| 3 | C$_6$H$_5$ | C$_6$H$_4$CH$_3$(2) | Cl | SC | 0/10(10T) | 0/5(5T) | 2/10(8T) | 2/5(1T) | 4/10 | 0/5 |  |
| 4 | C$_6$H$_5$ | C$_6$H$_4$CH$_3$(4) | Cl | SC | 0/10(10T) | 2/5(3T) | 10/10 | 5/5 | 2/10 | 0/5 |  |
|  |  |  |  | O | 0/10(4T)* | 0/5* | 0/10 | 0/5 | 0/10 | 0/5 |  |
| 5 | C$_6$H$_5$ | C$_6$H$_4$CH$_3$(2) | Br | SC | 0/5(5T) | 0/5(5T) | 0/10(10T) | 0/5(1T)* | 0/10 | 0/5 |  |
|  |  |  |  | O | 0/10(10T) | 0/5* | 0/10 | 0/5 | 0/10 | 0/5 |  |
| 6 | C$_6$H$_5$ | C$_6$H$_4$CH$_3$(4) | Br | SC | 0/5(5T) | 0/5(5T) | 0/5(2T)* | 0/5 | 0/5 | 0/5 | 0/5 |
|  |  |  |  | O | 10/10(10T) | 0/10(1T)* | 0/10 | 0/5 | 0/10 | 0/5 |  |
| 7 | C$_6$H$_5$ | C$_6$H$_4$OC$_2$H$_5$(4) | Cl | SC | 0/10(10T) | 0/5(5T) | 4/10(6T) | 3/5(1T) | 0/10 | 0/5 |  |
| 8 | C$_6$H$_5$ | C$_6$H$_4$CF$_3$(4) | Cl | SC | 0/10(10T) | 2/5(3T) | 2/10(2T) | 1/5 | 0/10 | 0/5 |  |
|  |  |  |  | O | 0/5(5T) | 0/5(3T) | 0/5(1T) | 0/5 | 0/5 | 0/5 |  |

Table I.-continued

Benzyl Triphenyl Phosphonium Salts Having Activity Against *Trypanosoma rhodesiense* Infections of Mice
$(AR)_3 PCH_2R\ X^-$

| Example Number | AR | R | X | Route[a] | No. Cured/No. Treated with Compound, in mg/kg |  |  |  |  |  |  |
|---|---|---|---|---|---|---|---|---|---|---|---|
| | | | | | 424 | 212 | 106 | 53 | 26.5 | 13.3 | 6.65 |
| 9 | $C_6H_5$ | $C_6H_4CO_2CH_3(2)$ | Br | SC | | | 2/10(8T) | 2/5(3T) | 0/10 | 0/5 | 0/10 |
| 10 | $C_6H_5$ | $C_6H_2OH(4)$-$tBu_2(3,5)$ | Br | SC | 0/10* | 0/5* | 0/10* | 0/5 | 0/10 | 0/5 | |
| | | | | O | 0/10* | 0/5 | 0/10 | 0/5 | 0/10 | 0/5 | |
| 11 | $C_6H_5$ | $C_9H_6N^c$ | Br | SC | 0/10(10T) | 1/5(3T) | 6/10 | 0/5 | 0/10 | 0/5 | |

Legend:
[a] route of administration to test animals: SC, subcutaneous; O, oral;
[b] T indicates death attributed to drug toxicity;
[c] denotes 8-quinolyl grouping;
*denotes activity, i.e., at least 100% increase in mean survival time of test animals when compared to infected, untreated controls.

EXAMPLE 12

3,4-Dichlorobenzyl triphenylphosphonium chloride: Anti-Trypanosomal Activity.

The phosphonium salt exhibited activity at dosage levels of 26.5, 40 and 53 mg/kg per body weight of mice. At a dosage level of 13.3 mg/kg, the mean survival time for the test animals did not sufficiently exceed the mean survival time for the control animals to exhibit activity. At dosages of over 100 mg/kg, toxicity resulted.

Table III

| DOSE | MSTT | MSTC | T-C | TOX | MSTX | CURES |
|---|---|---|---|---|---|---|
| 40 | 9.4 | 4.1 | 5.3 | 0 | 0 | 0 |
| 160 | 13.2 | 4.1 | 9.1 | 0 | 0 | 0 |
| 640 | 22.0 | 4.1 | 17.9 | 0 | 0 | 4 |
| 20 | 5.0 | 4.2 | 0.8 | 0 | 0 | 0 |
| 40 | 9.4 | 4.2 | 5.2 | 0 | 0 | 0 |
| 80 | 12.2 | 4.2 | 8.0 | 0 | 0 | 0 |
| 160 | 13.4 | 4.2 | 9.2 | 0 | 0 | 0 |
| 320 | 15.0 | 4.2 | 10.8 | 0 | 0 | 2 |
| 640 | 0.0 | 4.2 | 0.0 | 0 | 0 | 5 |

Table IV

Benzyl Triaryl Phosphonium Salts Having Activity Against *Trypanosoma rhodesiense* Infections of Mice
$(AR)_3 P^+CH_2R\ X^-$

| Example Number | AR | R | X | Route[a] | No. Cured/No. Treated with Compound, in mg/kg |  |  |  |  |  |  |
|---|---|---|---|---|---|---|---|---|---|---|---|
| | | | | | 424 | 212 | 106 | 53 | 26.5 | 13.3 | 6.65 |
| 14 | $C_6H_4CH_3(2-)$ | $C_6H_5$ | Cl | SC | 0/5(5T)[b] | | 0/10(10T) | 3/5(2T) | 6/10 | 0/5* | |
| | | | | O | 4/10(6T) | 4/5(1T) | 0/10* | 0/5 | 0/10 | 0/5 | |
| 15 | $2[C_6H_4CH_3-(2-)]C_6H_5^c$ | $C_6H_5$ | Cl | SC | 0/5(5T) | 0/5(5T) | 6/15(9T) | 8/10 | 12/15 | 0/10 | 0/10 |
| | | | | O | | 0/5(5T) | | 0/5 | | 0/5 | |
| 16 | $C_6H_4CH_3(2-)$ $2[C_6H_5]^c$ | $C_6H_5$ | Cl | SC | 0/5(5T) | | 0/10(10T) | 0/5(3T)* | 6/10 | 0/5 | 0/5 |
| | | | | O | 0/10(10T) | 1/5(2T) | 4/10 | 0/5 | 0/10 | 0/5 | |
| 17 | $C_6H_4CH_3(4-)$ $2[C_6H_5]^c$ | $C_6H_5$ | Cl | SC | 0/5(5T) | 0/5(5T) | 8/10(2T) | 3/5 | 0/10 | 0/5 | 0/5 |
| | | | | O | 0/10(10T) | 0/5* | 0/10* | 0/5 | 0/10 | 0/5 | |
| 18 | $C_6H_4CH_3(2-)$ | $C_6H_5$ | Cl | SC | 0/5(5T) | | 0/10(10T) | 2/5(1T) | 0/10 | 0/5 | |
| | | | | O | 0/5 | | 0/5 | | 0/5 | | |

Legend:
[a] route of administration to test animals: SC, subcutaneous; O, oral;
[b] T indicates death attributed to drug toxicity;
[c] differing aryl groups are indicated;
*denotes activity, i.e., at least 100% increase in mean survival time of test animals when compared to infected, untreated controls.

Table II

| DOSE | MSTT | MSTC | T-C | TOX | MSTX | CURES |
|---|---|---|---|---|---|---|
| 40 | 9.7 | 4.2 | 5.5 | 0 | 0 | 2 |
| 160 | 0.0 | 4.2 | 0.0 | 5 | 1 | 0 |
| 640 | 0.0 | 4.2 | 0.0 | 5 | 1 | 0 |
| 53 | 14.5 | 4.1 | 10.4 | 0 | 0 | 3 |
| 106 | 0.0 | 4.1 | 0.0 | 5 | 1 | 0 |
| 212 | 0.0 | 4.1 | 0.0 | 5 | 1 | 0 |
| 424 | 0.0 | 4.1 | 0.0 | 5 | 1 | 0 |
| 13.3 | 5.2 | 4.1 | 1.1 | 0 | 0 | 0 |
| 26.5 | 9.7 | 4.1 | 5.6 | 0 | 0 | 2 |

EXAMPLE 13

3,4-Dichlorobenzyl tris(3-methylphenyl)phosphonium chloride: Anti-Trypanosomal Activity.

As shown in Table III, the test compound exhibited anti-trypanosomal activities at all levels of dosage from 40 mg/kg to 640 mg/kg. In addition, in one test at a dose of 640 mg/kg, all five animals were cured.

EXAMPLE 19

Benzyl diphenyl 2-tolylphosphonium chloride: Anti-Trypanosomal Activity.

As shown in Table V, although toxicity was exhibited, the compound was shown to be active at dosage levels between 40 mg/kg and 160 mg/kg.

Table V

| DOSE | MSTT | MSTC | T-C | TOX | MSTX | CURES |
|---|---|---|---|---|---|---|
| 40 | 11.5 | 4.2 | 7.3 | 0 | 0 | 3 |
| 160 | 0.0 | 4.2 | 0.0 | 5 | 1 | 0 |
| 640 | 0.0 | 4.2 | 0.0 | 5 | 1 | 0 |
| 10 | 5.0 | 4.2 | 0.8 | 0 | 0 | 0 |
| 20 | 5.8 | 4.2 | 1.6 | 0 | 0 | 0 |
| 40 | 12.0 | 4.2 | 7.8 | 0 | 0 | 3 |
| 80 | 13.5 | 4.2 | 9.3 | 3 | 1 | 0 |
| 160 | 0.0 | 4.2 | 0.0 | 5 | 1 | 0 |
| 5.0 | 5.0 | 4.2 | 0.8 | 0 | 0 | 0 |
| 40 | 4.6 | 4.1 | 0.5 | 0 | 0 | 0 |
| 160 | 8.3 | 4.1 | 4.2 | 0 | 0 | 2 |
| 640 | 0.0 | 4.1 | 0.0 | 5 | 1 | 0 |
| 20 | 4.4 | 4.2 | 0.2 | 0 | 0 | 0 |
| 40 | 4.6 | 4.2 | 0.4 | 0 | 0 | 0 |
| 80 | 5.4 | 4.2 | 1.2 | 0 | 0 | 0 |
| 160 | 8.7 | 4.2 | 4.5 | 0 | 0 | 2 |

| Table V-continued | | | | | | |
|---|---|---|---|---|---|---|
| DOSE | MSTT | MSTC | T-C | TOX | MSTX | CURES |
| 320 | 13.0 | 4.2 | 8.8 | 2 | 1 | 1 |
| 640 | 0.0 | 4.2 | 0.0 | 5 | 1 | 0 |

EXAMPLE 20

Benzyl phenyl bis-(2-tolyl)phosphonium chloride: Anti-Trypanosomal Activity.

As shown in Table VI (below), anti-trypanosomal activity was exhibited at dosage levels of between 40 and 160 mg/kg, and 4 cures were exhibited in several tests at dosage levels of 40 and 80 mg/kg.

Table VI

| DOSE | MSTT | MSTC | T-C | TOX | MSTX | CURES |
|---|---|---|---|---|---|---|
| 40 | 10.0 | 4.2 | 5.8 | 0 | 0 | 0 |
| 160 | 0.0 | 4.2 | 0.0 | 3 | 1 | 2 |
| 640 | 0.0 | 4.2 | 0.0 | 5 | 1 | 0 |
| 10 | 5.0 | 4.2 | 0.8 | 0 | 0 | 0 |
| 20 | 5.2 | 4.2 | 1.0 | 0 | 0 | 0 |
| 40 | 12.0 | 4.2 | 7.8 | 0 | 0 | 4 |
| 80 | 14.0 | 4.2 | 9.8 | 0 | 0 | 4 |
| 160 | 0.0 | 4.2 | 0.0 | 3 | 1 | 2 |
| 320 | 0.0 | 4.2 | 0.0 | 5 | 1 | 2 |
| 10 | 5.2 | 4.1 | 1.1 | 0 | 0 | 0 |
| 20 | 5.6 | 4.1 | 1.5 | 0 | 0 | 0 |
| 40 | 12.0 | 4.1 | 7.9 | 0 | 0 | 4 |
| 80 | 13.0 | 4.1 | 8.9 | 0 | 0 | 4 |
| 160 | 0.0 | 4.1 | 0.0 | 3 | 1 | 2 |
| 5.0 | 4.2 | 4.1 | 0.1 | 0 | 0 | 0 |

What is claimed and desired to be secured is:

1. A method for treating African trypanosomiasis which comprises administering, either parenterally or perorally and using a pharmaceutically acceptable vehicle, a therapeutically effective amount of a phosphonium compound of the formula:

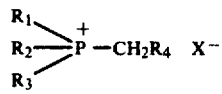

wherein $R_1$ through $R_4$ each represent phenyl or substituted phenyl and X represents halogen; and wherein the phosphonium compound is administered to a subject infected with a trypanosomal parasite.

2. The method of claim 1, wherein the phosphonium compound has the formula:

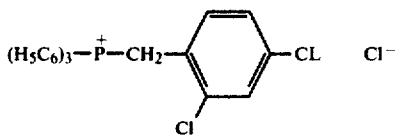

3. The method of claim 1, wherein the phosphonium compound has the formula:

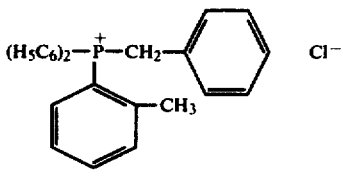

4. The method of claim 1, wherein the phosphonium compound has the formula:

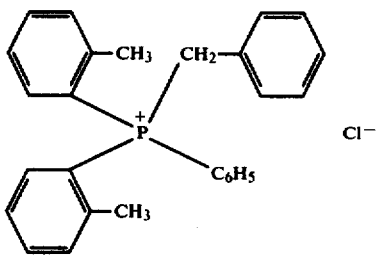

5. The method of claim 1, wherein the phosphonium compound has the formula:

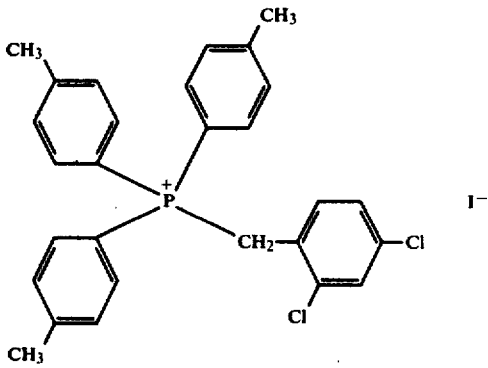

6. The method of claim 1, wherein said compound is administered subcutaneously.

7. The method of claim 1, wherein said compound is present in said vehicle in a quantity of at least about 40 mg/kg body weight of said subject to be treated.

* * * * *